United States Patent [19]

Delfour et al.

[11] Patent Number: 4,929,079
[45] Date of Patent: May 29, 1990

[54] OPTICAL GRANULOMETRY PROCESS AND DEVICES FOR BROAD MEASURING RANGES

[75] Inventors: André Delfour, Ramonville; Francois Falempin, St Michel Sur Orge; Jacques Isbert, Toulouse; Claude Sans, Massy, all of France

[73] Assignee: Office Natioanl D'Etudes Et De Recherches Aerospatiales styled O.N.E.R.A, Chatillon, France

[21] Appl. No.: 217,737

[22] Filed: Jul. 11, 1988

[30] Foreign Application Priority Data

Jul. 10, 1987 [FR] France .................. 87 09785

[51] Int. Cl.$^5$ ............................................ G01N 15/02
[52] U.S. Cl. ...................... 356/336; 364/525; 250/574
[58] Field of Search ............... 356/336, 335; 364/525, 364/555; 350/574

[56] References Cited

U.S. PATENT DOCUMENTS 4,274,741 6/1981 Cornillault .................. 356/336
4,622,642 11/1986 Bajard et al. ................ 364/555

OTHER PUBLICATIONS

Int'l. Conf. on Liquid Atomisation and Spray System: "Performance Comparison of Malvern Instruments Laser Differaction Drop Size Analyzers", by E. S. Hirleman et al., ICLASS 85, pp. IVA/3/1–IVA/3/14.

Primary Examiner—Leon Scott, Jr.
Attorney, Agent, or Firm—Lowe, Price, LeBlanc, Becker & Shur

[57] ABSTRACT

A granulometry device embodying the invention comprises a measuring probe and a micro-computer. The micro-computer provides digital filtering on a first discrete distribution function that is calculated by statistical inversion from a plurality of radiation measurements supplied by the probe and a theoretical radiation coefficient matrix thereby determining, after an iterative calculation, an optimum relation which should be satisfied by the nodes defining a discrete distribution function so as to offer a maximum correlation with uncertainty measurements. All the discrete distribution functions satisfying this relation are then calculated by statistical inversions. The mirco-computer provides an optimum statistical evaluation of the distribution of particles in a gas or liquid fluid.

12 Claims, 4 Drawing Sheets

OPTICAL GRANULOMETRY PROCESS AND DEVICES FOR BROAD MEASURING RANGES

BACKGROUND OF THE INVENTION

1. Field of the Invention

This invention relates to the granulometry field in general. More especially the invention relates to a granulometry process and devices for optical measuring sizes and concentrations of particles in suspension in a gaseous or liquid fluid.

2. Description of the Prior Art

At present in the granulometry field, measuring instruments with the highest performance make use of optical measuring processes. The existing instruments are of two types. Counting instruments requiring the presence of one single particle at a time in a measuring volume belong to a first type. Instruments sample analyzing the light scattering of a sample volume illuminated by a cloud of particles so as to determine a cloud particle size distribution function, belong to a second type.

The instruments of the first type, such as the so-called KNOLLENBERG instruments, use the properties of light scattering by a single particle. The main drawback of these instruments lies in the necessity of the presence of one single particle at a time in the measuring volume. In this way these instruments have limited performances and do not cover a clearly defined size measuring range.

The instruments of the second type use the FRAUNHOFFER approximation or the LORENZ-MIE theory to calculate the light scattering of a cloud of particles. The field of use of these instruments is limited to a voluminal concentration measuring range lying between $10^{-9}$ and $10^{-5}$. The size measuring range depends on the theorical diffusion model employed.

The chief instruments of the second type at present available on the market are those sold under the MALVERN trademark. These instruments make use of the FRAUNHOFFER approximation. The article by E. D. HIRLEMAN and L. G. DODGE entitled "Performance comparison of Malvern instruments laser diffraction drop size analyzers" and published in the 3rd "International Conference on Liquid Atomisation and Spray Systems" (ICLASS 85), pages IVA/3/1 to IVA/3/14, Institute of Energy, London, 1985, indicates their performances.

The particle size distribution is only considered to be very well estimated by the MALVERN instruments for particles having a diameter above 5 $\mu$m. Moreover, a considerable drawback to these instruments is their lack of accuracy as soon as the distribution function to be measured cannot be modeled by a simple ROSIN-RAMMLER or log-normal type function. This lack of accuracy is due to the distribution function calculation process requiring a matricial inversion and an estimation by the method of least squares entailing an unstable result.

Moreover, the different instruments available have a form and dimensions which are not suited to measure the sizes and concentrations of particles in a fluid flow. In fact, an unsuitable form and oversized dimensions disturb the flow of the fluid and modify the measurements. These instruments are unadapted to be carried by a moving vehicle, for example by an aircraft, in order to determine the size distribution of droplets in suspension in the air.

OBJECTS OF THE INVENTION

The main object of this invention is to provide a granulometry process thereby improving the performances obtained by the granulometry devices in the prior art.

Another object of this invention is to provide a granulometry device adapted to determine the size distribution of particles in a fluid flow.

SUMMARY OF THE INVENTION

For this purpose, there is provided a process for evaluating a size distribution of particles in a fluid from measurements of scattered radiation along predetermined spacial directions in a finished integer number P by a sample of said fluid illuminated by an incident light beam. From a radiation measuring vector having, as components, mean radiations along the P directions determined after several successive measurements and from a matrix of theoretical radiation coefficients is calculated a first estimation of the distribution expressed by a first discrete distribution function contained in a mathematical envelope function of predetermined type and respectively fixing concentration values at size nodes for which the first function is defined, the size nodes being distributed thereby satisfying a recursive relation of predetermined type.

The first function is taken as starting data to determine, by an iterative calculation involving digital filterings, an optimum recursive relation to which the nodes of a discrete distribution function should satisfy whereby the discrete distribution function nodes be distributed in such a way that the discrete distribution function offers maximum correlation with a discrete measurement uncertainty function resulting from several successive radiation measurements in the P directions. All the discrete distribution functions compatible with the measurement uncertainties and whose nodes satisfy the optimum recursive relation are then calculated from the radiation measuring vector and the matrix thereby deducing an optimum statistical evaluation of the size distribution researched.

This invention further provides a device for implementing the process, i.e., for evaluating a size distribution of particles in a fluid from measurements of scattered radiation along predetermined spacial directions in a finished integer number P by a sample of the fluid illuminated by an incident light beam. The evaluating device comprises:

means for producing the light beam designed to illuminate the fluid sample, means for measuring the radiation scattered along the P spacial directions thereby supplying radiation measurements, means for converting the radiation measurements into digital measurements, means having stored a program and a theoretical radiation coefficient matrix for processing the digital radiation measurements and calculating an optimum statistical evaluation of the size distribution researched, and means for displaying the optimum statistical evaluation calculated.

According to other aspects of this invention, in a device for evaluating the size distribution of particles in a flow of a fluid, the producing means, the measuring means and the converting means are included in a measuring probe in the device. The measuring probe further comprises means for sampling a part of the fluid flow and conveying the fluid flow into the probe, and optical reflection means for directing the light beam produced by the producing means to the sample and directing the radiation scattered by the sample to the measuring means. The producing means and the measuring means are remote from the sample and located downline from the sample in the direction of the flow, whereby the probe has a predetermined form not disturbing the flow to be analyzed in the vicinity of the sample.

The process embodying the invention authorizes high performances. The size measuring range is from 0.1 μm to 300 μm; the voluminal concentration measuring range is from 0.2 to $8.10^{-6}$. The distribution function is determined in practically real time with accuracy greater than or equal to 10%.

The granulometry devices as embodied by the invention are especially well adapted to be carried by an aircraft or to be used in an aerodynamic wind tunnel. The devices provide for the measurement in a flow animated by a speed from Mach 0 to Mach 0.9.

In sealed version, a device embodying the invention can be immersed in a liquid, such as water, so as to research diameters and concentrations of air bubbles for example.

BRIEF DESCRIPTION OF THE DRAWING

The foregoing and other objects, features and advantages of the invention will be apparent from the following detailed description of several embodiments of the invention with reference to the corresponding accompanying drawings in which.

DESCRIPTION OF THE PREFERRED EMBODIMENTS

Figure 1:
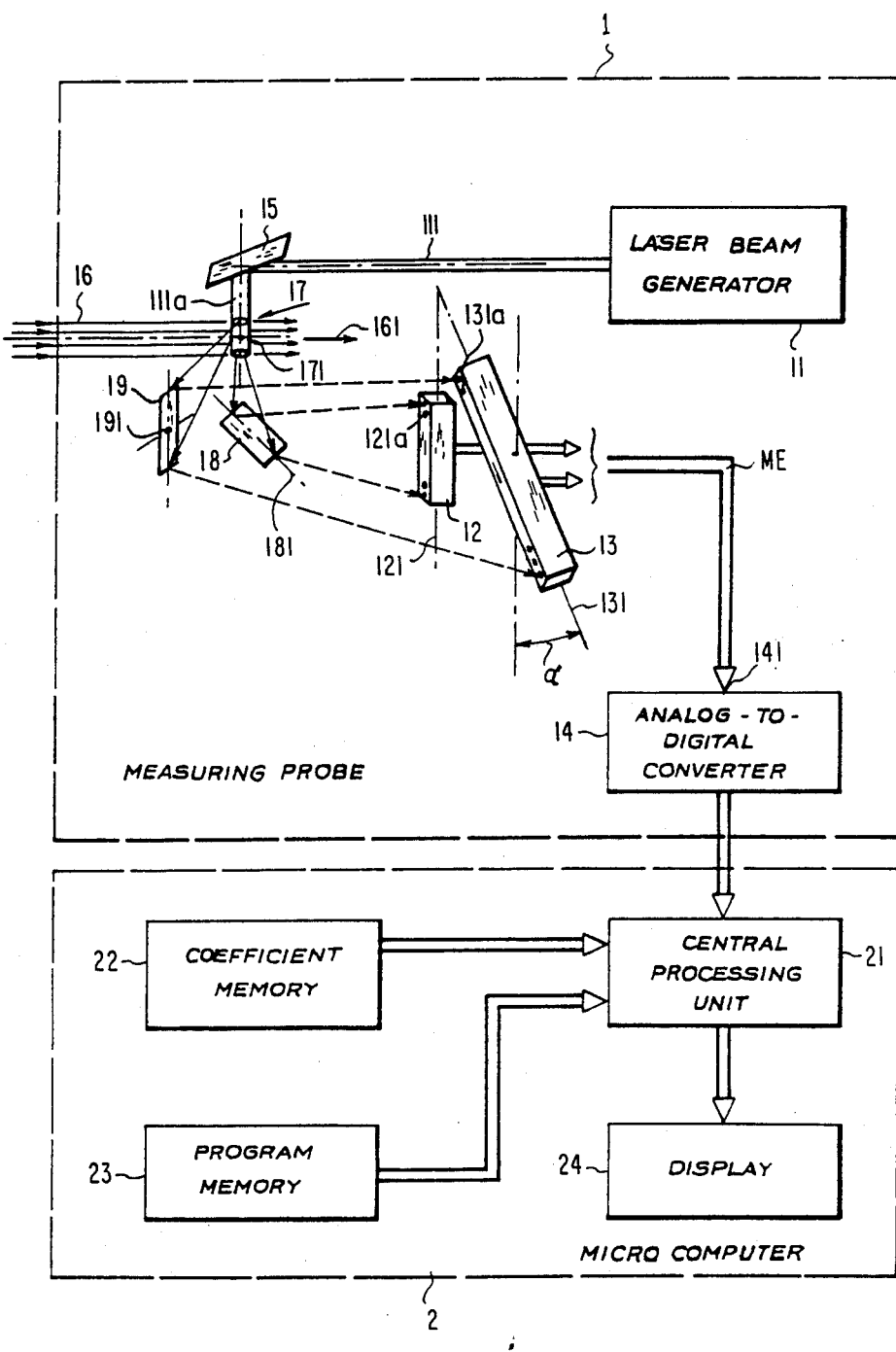
FIG. 1 is a schematic functional bloc diagram of a granulometry device embodying the invention.

Referring to FIG. 1, the device embodying the invention consists of a measuring probe 1 and a micro-computer 2.

The measuring probe 1 basically comprises a laser beam generator 11, first and second radiation measuring strips 12 and 13, and analog to digital converter 14.

The laser beam generator 11, for example gas type, provides a polarized and expanded laser beam 111.

The laser beam 111 is reflected into a reflected laser beam 111a by a plane mirror, or total reflection prism 15, so as to modify the propagation direction of the beam and make it cross a fluid 16 containing particles in suspension having different diameters. Fluid 16 is directed into probe 1 along a predetermined direction of flow 161 and is crossed through perpendicularly by the reflected laser beam 111a. The intersection of beam 111a and fluid 16 is a substantially cylindrical volume 17. Volume 17 forms a measuring volume that is predetermined by the choice of the laser beam 111 diameter and by the sizing of a semi-circular hollow guide 172 (FIG. 4) being part of a plate in probe 1 directing the flow of the fluid 16.

The measuring volume 17 contains a plurality of substantially spherical particles having different diameters Φ that are distributed in accordance with a size distribution function f(Φ) whose evaluation is the purpose of the measurement. Each of the particles in the measuring volume 17 forms an element diffracting the laser beam 111a and scatters a light wave having the same wavelength as that of the laser beam.

With the strict LORENZ-MIE theory it is possible to calculate, for any given direction of the space, the effective differential quantity of light radiation scattered in this direction by a spherical particle illuminated by a light wave. This differential quantity is a function of a complex refraction index m of the particle and of the diameter Φ thereof.

For a cloud of particles, the effective light radiation scattered by this cloud along a direction d of the space is, to the infinite, equal to the sum of the differential quantities scattered in the same direction d by the different particles making up the cloud. The light radiation scattered by a cloud of particles along a direction d of the space is provided by the integral equation:

$$b(d) = \int_{\Phi_{mini}}^{\Phi_{maxi}} K(d,\Phi,m) \cdot f(\Phi) \cdot d\Phi,$$

where b(d) denotes the effective light radiation scattered by the cloud along direction d, f(Φ) is the size distribution function of the cloud, K(d, Φ, m) is a radiation function according to the LORENZ-MIE theory providing for each of the cloud particles that is defined by its diameter Φ and its refraction index m, the differential quantity of light radiation that the particle scattered along the direction d, and where $\Phi_{mini}$ and $\Phi_{maxi}$ define a diameter range in which the diameter Φ of any particle of the cloud lies.

The radiation measuring strips 12 and 13 are illuminated by the radiation scattered by the measuring volume 17. Plane returning mirrors, or prisms, 18 and 19 respectively associated to strips 12 and 13 are provided in probe 1 so as to reflect parts of the radiation scattered by volume 17 to strips 12 and 13. Mirror 18 is placed opposite mirror 15, in relation to the flow direction 161 of fluid 16, and receives a part of the radiation scattered by the measuring volume 17 observed along to the propagation direction of laser beam 111a, this direction of propagation being perpendicular to the polarisation plane of the beam. Strip 12 is aligned with an axis 121 parallel to the propagation direction of laser beam 111a and is oriented so as to be illuminated by the radiation reflected by mirror 18. Mirror 19 is placed perpendicularly to the polarisation plane of beam 111a and receives the radiation scattered by the measuring volume 17 and observed along a direction perpendicular to the propagation direction of beam 111a. Strip 13 is aligned with an axis 131 inclined at a predetermined angle α in relation to the propagation direction of laser beam 111a so as to provide for a higher number of measurements. Strip 13 is oriented towards mirror 19 and is illuminated by the radiation reflected from mirror 19.

Strips 12 and 13 respectively include pluralities of aligned photosensitive cells, such as phototransistors, 121a and 131a forming the same number of radiation measuring receivers. Strips 12 and 13 measure the radiation scattered by measuring volume 17 respectively according to first and second groups of measuring directions d comprised in first and second measuring planes, respectively. The first measuring plane corresponding to strip 12 is perpendicular to the polarisation plane of laser beam 111a and passes through axis 121 of strip 12 and asymmetry axis 181 of mirror 18. The second measuring plane corresponding to strip 13 passes through symmetry centre 191 of mirror 19 and a symmetry centre 171 of measuring volume 17 and is inclined by angle α in relation to a plane that passes through the same symmetry centres 191 and 171 and that is perpendicular to the polarisation plane of laser beam 111a.

Measuring strips 12 and 13 provide measuring vectors ME each consisting of P measurements, where P is typically equal to 32, respectively directed along P different directions $d_1$ to $d_p$ included in the first and second measuring planes.

Parallel inputs 141 of the analog-to-digital converter 14 receive the measuring vectors ME and supply them in digital form to micro-computer 2.

Micro-computer 2 comprises a central processing unit 21, a coefficient memory 22, a program memory 23, and display means 24.

The central processing unit 21 receives the digitalized measuring vectors ME supplied by converter 14 of probe 1 and processes them using coefficients memorised in memory 22, according to a computation and processing program memorized in memory 23, thereby determining the size distribution function $f(\phi)$ of the particles contained in the measuring volume 17.

Generally speaking, the real size distribution functions have know natural waveforms and it can be considered that any size distribution function to be determined can be modeled by a sum of mathematical functions of analogous type. According to the process of the invention, it is considered as acquired that a size distribution function of a particle cloud can be modeled by a sum of known exponential mathematical functions of type B-spline. These functions are defined by slot function convolution products and are represented by monotone curves with a minimum second derivate; their value is nul outside the interval lying between the first and fifth nodes. The distribution function $f(\phi)$ researched can be expressed by the following equation:

$$f(\phi) = \sum_{j=1}^{j=J} a_j \cdot S_j(\phi),$$

where j is an integer index varying between 1 and a maximum value J. Functions $S_j(\phi)$ are B-spline functions, and the multiplier coefficients $a_j$ are positive real coefficients respectively associated to functions $S_j(\phi)$.

Memory 22 memorises a coefficient matrix T comprising P.Q coefficients, $t_{11}$ to $t_{PQ}$, where Q is a predetermined integer having a high value typically equal to 150. Coefficients t of matrix T are determined theorically by applying the LORENZ-MIE theory.

A coefficient $t_{pq}$ of matrix T, where p and q are integers lying respectively between 1 and P and between 1 and Q, represent a weight of radiation in the direction $d_p$ for a particle having a diameter $\phi_q$.

Matrix T is calculated via a computation program stored for this purpose in program memory 23 of microcomputer 2, for a given refraction index m corresponding to the nature of the particle cloud. Matrix T represents, in discretized form, the relation that links the radiation b scattered in space by measuring volume 17 to the size distribution function $f(\phi)$ for particles included in measuring volume 17. The following equality can be expressed:

$$B = T.F,$$

where B is a radiation vector having P=32 components $b_1$ to $b_p$ that represent the radiations scattered by measuring volume 17 along the P=32 directions $d_1$ to $d_p$ in the first and second measuring planes respectively, and F is a vector representing a discrete form of distribution function f( ) and having Q=150 components $f_1$ to $f_Q$ that are equal respectively to the Q=150 respective concentrations of Q=150 particles having different diameters in measuring volume 17.

It results from the above equality that it is possible to calculate vector F representing a new discrete from of the distribution function $f(\phi)$ and having a maximum of J=31 components, where J is a predetermined integer, knowing vector B and inverting a degenerated form U of matrix T.

Unit 21 calculates a statistical estimation of vector B from plural successive measuring vectors ME provided by probe 1 and by means of a correction coefficient table. Each of the cells 121a, 131a of strips 12 and 13 having a specific response curve, the correction coefficient table contains coefficients to be applied to the measurements provided by cells 121a, 131a in order to determine the corresponding radiations. A mean radiation vector Bm and a corresponding standard deviation vector σB are calculated by unit 21. Vectors Bm and σB each comprise P=32 components, respectively $bm_1$ to $bm_p$ and $\sigma b_1$ to $\sigma b_p$.

As from mean vector Bm and matrix U, the central processing unit 21 determines a vector $Fa_0$ qualifying a distribution and representing the corresponding coefficients $a_j$ of the J←31 cubic B-spline functions having nodes $\phi_{11}$ to $\phi_{JN}$ that are defined at the origin by the following relations:

$$\phi_{11} = mini,$$

$$\phi_{JN} = \phi_{maxi}$$

$$j, n + 1 = C \cdot \phi_{j,n}, \text{ and}$$

$$j + 1, n = C \cdot \phi_{j,n},$$

where $\phi_{mini}$ and $\phi_{maxi}$ are predetermined values delimiting an interval in which lie all the values of the nodes, where n and j are integers varying respectively between 1 and N and between 1 and J, and where C is a multiplier coefficient having a value $C_0$ for the vector $Fa_0$.

Matrix T comprising P.Q coefficients is transformed into matrix U comprising P.J coefficients u calculated from the relation:

$$u_{pj} = \int_{\Phi_{j1}}^{\Phi_{jN}} K(d, \Phi, m) \cdot S_j(\Phi) \cdot d\Phi,$$

Figure 2:
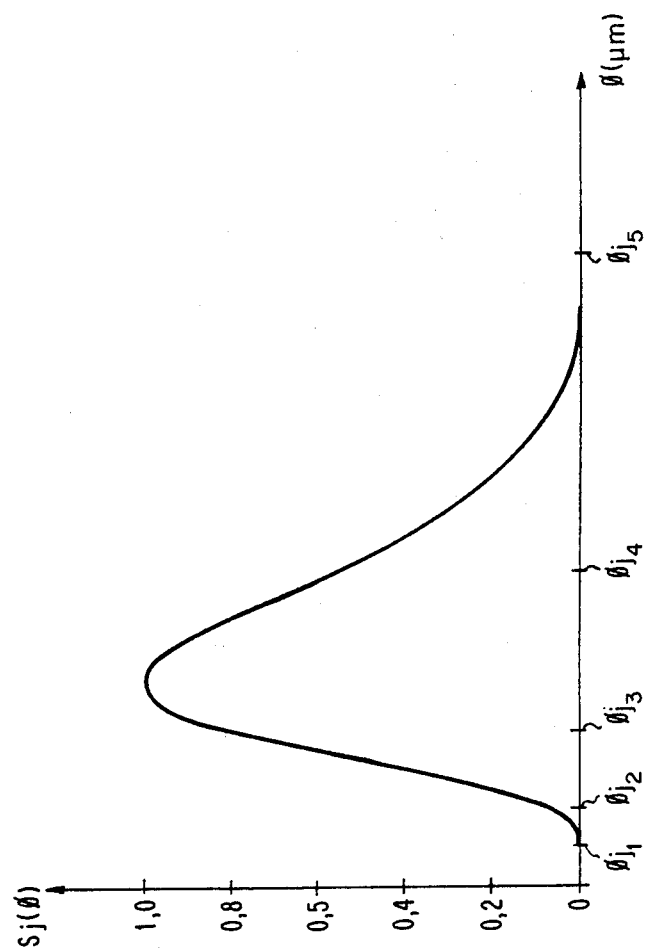
FIG. 2 shows a mathematical function used according to the invention process in order to modele a size distribution function researched.

A function $S_j(\phi)$ is shown in FIG. 2; $S_j(\phi)$ is defined from a typical number of nodes N equal to 5. The vector $Fa_0$ from vector Bm and matrix U is calculated according to statistical inversion processes conventional in the prior art and known to those skilled in the art. Vector $Fa_0$ can be an optimum solution determined by the calculation of a minimum mean quadratic deviation in relation to an exact mathematical solution equal to $Bm.U^{-1}$. The modeled distribution vector $Fa_0$ thus calculated is an unstable solution. The multiplier coefficient C between the nodes of vector $Fa_0$ has a calculated value $C_0$ which can be optimized so as to define vector $Fa_0$ by nodes for which vector $Fa_0$ is correlated maximally with a vector of measurement uncertainties.

According to the process embodying the invention, a digital filtering is obtained to determine an optimum value $C_{opt}$ of multiplier coefficient C. Several convolution products $PC_{01}$, $PC_{02}$, ... $PC_{0I}$, where I is a predetermined integer, are calculated between a standard deviation vector $\sigma B = U^{-1} . \sigma B$ and respectively several vectors $Fa_{01}$, $Fa_{02}$, ... $Fa_{0I}$. The vectors $Fa_{01}$ to $Fa_{0I}$ are deduced from vector $Fa_0$ by varying the multiplier coefficient C around value $C_0$. Values $C_{11}$ to $C_{1I}$ around value $C_0$ of multiplier coefficient C correspond respectively to vector $Fa_{01}$ to $Fa_{0I}$. Amongst the convolution products $PC_{01}$ to $PC_{0I}$ corresponding respectively to values $C_{11}$ to $C_{1I}$ of multiplier coefficient C, a convolution product has a maximum value. A value $C_1$ of multiplier coefficient C corresponds to this convolution product with maximum value. The value $C_1$ of multiplier coefficient C is an intermediate optimum value to which a vector $Fa_1$ amongst the vectors $Fa_{01}$ to $Fa_{0I}$ corresponds.

In the case in which value $C_1$ is greater than or equal to value $C_0$ of the multiplier coefficient C, vector $Fa_1$ is legitimately interpolated from vector $Fa_0$, because it comprises a number of components, corresponding to the nodes of the B-spline functions, at most equal to that of vector $Fa_0$ and therefore only carries information already initially contained in vector $Fa_0$. In other words, the frequency spectrum of the discrete function corresponding to vector $Fa_1$ is included in the frequency spectrum of the discrete function corresponding to vector $Fa_0$. Value $C_1$ is in this case the researched optimum value $C_{opt}$ of multiplier coefficient C.

In the event in which value $C_1$ is lower than value $C_0$ of multiplier coefficient C, vector $Fa_1$ comprises a greater number of components than vector $Fa_0$ and is not a legitimate interpolation of vector $Fa_0$. Another modeled distribution vector $Fb_0$ representing function $f(\phi)$ and whose components correspond to nodes of B-spline functions linked by value $C_1$ of multiplier coefficient C, is calculated by the central processing unit 21 from the mean vector Bm and the matrix U, by statistical inversion. Vector $Fb_0$ is then processed in a similar way to vector $Fa_0$.

The determination of the optimum value $C_{opt}$ of multiplier coefficient C requires an iterative calculation process, as described above. In practice value $C_{opt}$ is typically obtained from two or at most three iterations.

The optimum value $C_{opt}$ of multiplier coefficient C being determined, the central processing unit 21 calculates, by statistical inversion and shifting the nodes of the B-spline functions, all the distribution vectors F defined from the value $C_{opt}$ of multiplier coefficient C and compatible with vectors Bm and $\sigma B$. An optimum vector $F_{opt}$ amongst all the vectors F offers a minimum mean quadratic deviation in relation to the mean solution $U^{-1}.Bm$. Vector $F_{opt}$ represents optimally, the size distribution function $f(\phi)$ of the particles in volume 17.

The central processing unit 21 provides the result of the calculations to the display means 24. The modeled function $f(\phi)$ may also be displayed in statistical form calculated from all the vectors F.

Figure 3:
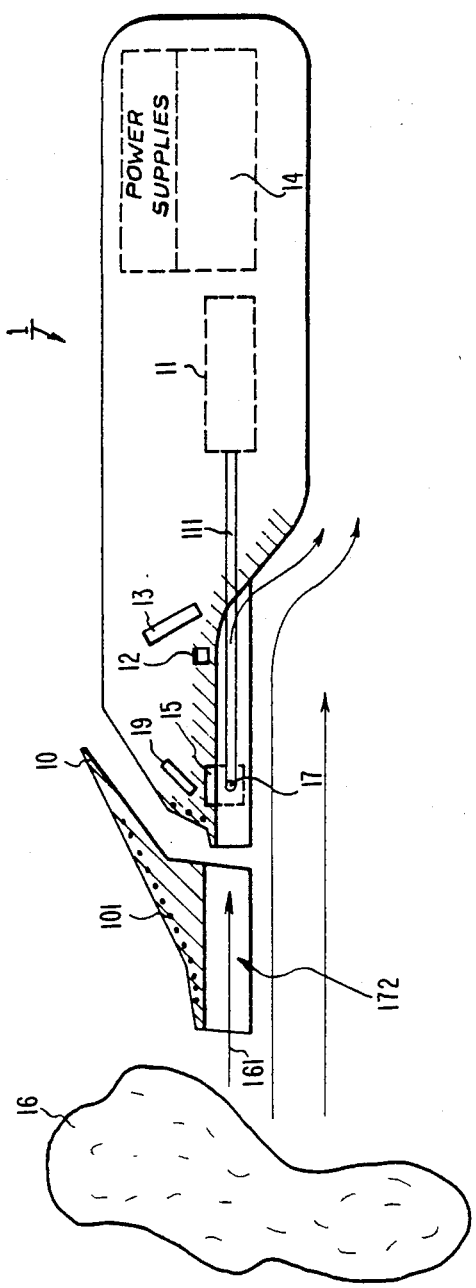
FIG. 3 shows the location of different members in a measuring probe in a granulometry device embodying by the invention.
Figure 4:
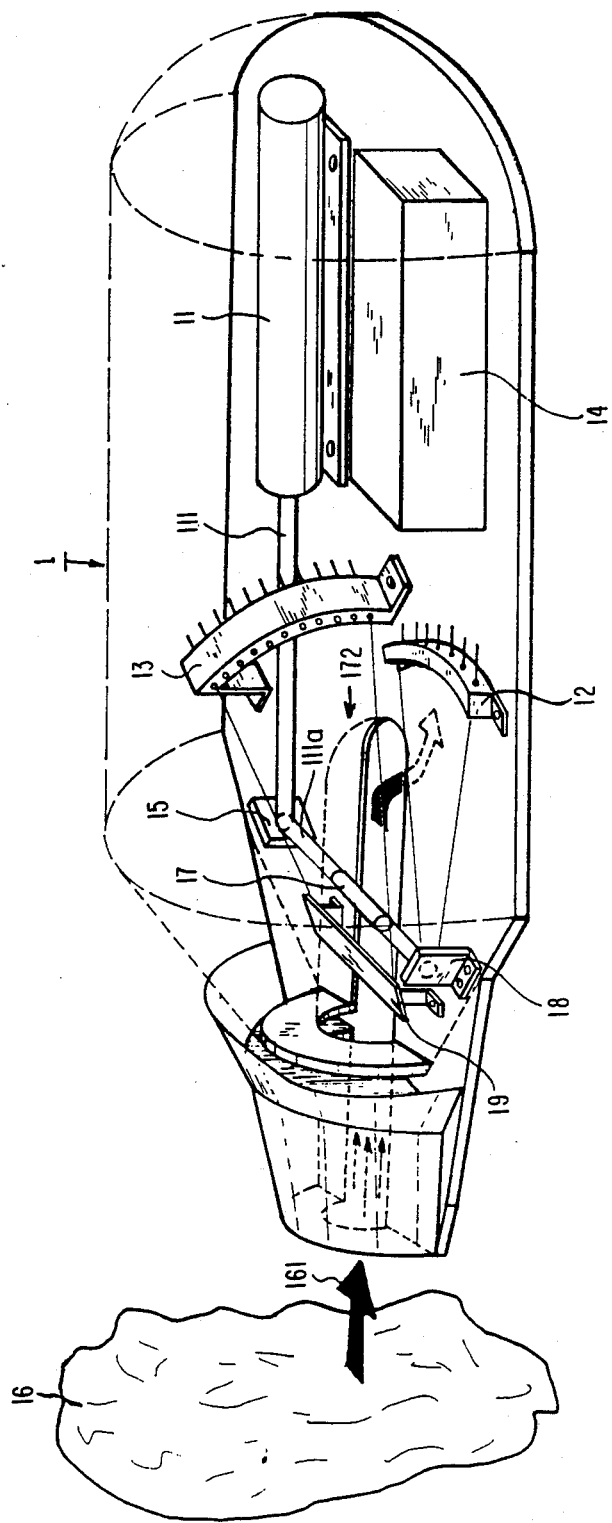
FIG. 4 is a perspective view of a measuring probe embodying the invention.

As shown in FIGS. 3 and 4, mirrors 15, 18 and 19 are provided in the measuring probe 1 so as to enable a correct positioning of the laser beam generator 11, strips 12 and 13, converter 14 and respective power supplies, not shown in FIG. 1. These different members are placed downline, according to the flow direction 161 of fluid 16, from the measuring point materialised by volume 17 so as not to disturb the fluid flow to be measured.

All the members of the measuring probe are secured to a covered mounting plate. This mounting plate is designed so as to convey the flow of the fluid at right angles from the laser beam by the semi-circular hollow guide 172, without channelling it which would create risks of deteriorating the sizes of the particles or droplets by modifying the flow characteristics. With the same purpose, a deflector 10, shown in FIG. 3, equipped with a limit layer trap, is placed in front of probe 1 so as to minimise the disturbances that the presence of the probe might generate within the flow to be analyzed. Probe 1 being designed to operate in variable temperature conditions, deflector 10 is provided with heating elements 101, such as resistors thereby ensuring the integrity of its form during variations in temperature.

What is claimed is:

1. A process of evaluating a size distribution of particles in a fluid from measurements of scattered radiation along predetermined spacial directions in a finished integral number P by a sample of said fluid illuminated by an incident light beam, said process comprising:

from a radiation measuring vector having, as components, mean radiations along said P directions determined after several successive measurements and from a matrix of theoretical radiation coefficients, calculating a first estimation of said distribution expressed by a first discrete distribution function contained in a mathematical envelope function of predetermined type and respectively fixing concentration values at size nodes for which said first function is defined, said size nodes being distributed thereby satisfying a recursive relation of predetermined type, determining by an iterative calculation involving digital filterings an optimum recursive relation to which the nodes of a discrete distribution function should satisfy, said determining step being performed in response to said first function being taken as starting data, whereby said discrete distribution function nodes are distributed in such a way that said discrete distribution function offers maximum correlation with a discrete measurement uncertainty function resulting from several successive radiation measurements in said P directions, and then calculating from said radiation measuring vector and said matrix all the discrete distribution functions compatible with said measurement uncertainties, the nodes of which satisfy said optimum recursive relation, thereby deducing an optimum statistical evaluation of said size distribution.

2. The process of claim 1, wherein said radiation coefficients of said matrix are determined from the LORENZ-MIE theory.

3. The process of claim 1, wherein said mathematical envelope function is a sum of B-spline type mathematical functions.

4. The process of claim 1, wherein said recursive relation of predetermined type links any two successive nodes of a discrete distribution function by a multiplier coefficient.

5. A device for evaluating a size distribution of particles in a fluid from measurements of scattered radiation along predetermined spacial directions in a finished integral number P by a sample of said fluid illuminated by an incident light beam, said device comprising
  means for producing said light beam for illuminating said fluid sample,
  means for measuring said radiation scattered along said P spacial directions thereby supplying radiation measurements,
  means for converting said radiation measurements into digital measurements,
  means having a program and a theoretical radiation coefficient matrix stored therein for processing said digital radiation measurements and calculating an optimum statistical evaluation of said size distribution, and
  means for displaying said calculated optimum statistical evaluation.

6. The device claimed in claim 5, wherein said producing means is a laser beam generator.

7. The device claimed in claim 5, wherein said measuring means comprises measuring strips each having a plurality of aligned measuring photosensitive cells.

8. The device claimed in claim 5, wherein said processing and calculating means is a micro-computer.

9. The device claimed in claim 5, wherein said producing means, said measuring means and said converting means are included in a measuring probe in said device.

10. The device claimed in claim 9, wherein said measuring probe further comprises means for sampling a flowing part of said fluid and conveying said fluid flow into said probe, and optical reflection means for directing said light beam produced by said producing means to said sample and directing said radiation scattered by said sample to said measuring means,
  said producing means and said measuring means being remote from said sample and located downstream from said sample in the direction of said flow, whereby said probe has a predetermined form such that said flow to be analyzed is not disturbed in the vicinity of said sample.

11. The device claimed in claim 10, wherein said sampling and conveying means comprises a semi-circular hollow guide and a deflector including a limit layer trap, heating resistors being sunk in said deflector, thereby ensuring form integrity of said deflector during temperature variations.

12. The device claimed in claim 10, wherein said optical reflection means includes total reflection members.

* * * * *